US006591844B2

(12) United States Patent
Barlow et al.

(10) Patent No.: US 6,591,844 B2
(45) Date of Patent: Jul. 15, 2003

(54) ELASTOMERIC MONOFILAMENT DENTAL TAPES

(75) Inventors: David Barlow, Edinburgh (GB); Dale G. Brown, Wharton, TX (US); Ian Roberts, Pencaitland (GB); Ira D. Hill, Locust, NJ (US); James McKenzie Hill, St Boswells (GB)

(73) Assignee: Peri-Deat Limited, Scotland (GB)

( * ) Notice: Subject to any disclaimer, the term of this patent is extended or adjusted under 35 U.S.C. 154(b) by 0 days.

(21) Appl. No.: 09/935,906

(22) Filed: Aug. 23, 2001

(65) Prior Publication Data
US 2002/0144704 A1 Oct. 10, 2002

Related U.S. Application Data

(60) Provisional application No. 60/281,667, filed on Apr. 5, 2001, and provisional application No. 60/263,220, filed on Jan. 1, 2001.

(51) Int. Cl.[7] ............................................... A61C 15/00
(52) U.S. Cl. ....................................................... 132/321
(58) Field of Search ............................... 132/321, 329; 427/2.29; 264/172.17, 172.18

(56) References Cited

U.S. PATENT DOCUMENTS

| | | | |
|---|---|---|---|
| 2,667,443 A | 1/1954 | Ashton | 167/93 |
| 2,772,205 A | 11/1956 | King | 167/93 |
| 3,699,979 A | 10/1972 | Muhler et al. | 132/89 |
| 3,800,812 A | 4/1974 | Jaffe | 132/89 |
| 3,838,702 A | 10/1974 | Standish et al. | 132/89 |
| 3,897,795 A | 8/1975 | Engel | 132/89 |
| 3,928,618 A | 12/1975 | Bauman | 424/311 |
| 3,943,949 A | 3/1976 | Ashton et al. | 132/89 |
| 4,029,113 A | 6/1977 | Guyton | 132/91 |
| 4,033,365 A | 7/1977 | Klepak et al. | 132/89 |
| 4,338,275 A * | 7/1982 | Carr | 264/172.17 |
| 4,414,990 A | 11/1983 | Yost | 132/91 |
| 4,627,975 A | 12/1986 | Lynch | 424/49 |
| 4,638,823 A | 1/1987 | Newman et al. | 132/91 |
| 4,776,358 A | 10/1988 | Lorch | 132/321 |
| 4,911,927 A | 3/1990 | Hill et al. | 424/443 |
| 4,974,615 A | 12/1990 | Doundoulakis | 132/321 |
| 4,986,288 A | 1/1991 | Kent et al. | 132/321 |
| 5,033,365 A | 7/1991 | Rao et al. | 99/349 |
| 5,033,488 A | 7/1991 | Curtis et al. | 132/321 |
| 5,098,711 A | 3/1992 | Hill et al. | 424/401 |
| 5,115,002 A * | 5/1992 | Van Helden et al. | 524/91 |
| 5,165,913 A | 11/1992 | Hill et al. | 424/49 |
| 5,209,251 A | 5/1993 | Curtis et al. | 132/321 |
| 5,220,932 A | 6/1993 | Blass | 132/321 |
| 5,357,990 A | 10/1994 | Suhonen et al. | 132/321 |
| 5,423,337 A | 6/1995 | Ahlert et al. | 132/321 |
| 5,433,226 A | 7/1995 | Burch | 132/321 |
| 5,479,952 A | 1/1996 | Zachariades et al. | 132/321 |
| 5,503,842 A | 4/1996 | Fazan et al. | 260/621 |
| 5,518,012 A | 5/1996 | Dolan et al. | 132/321 |
| 5,558,901 A | 9/1996 | Gilligan et al. | 427/2.29 |
| RE35,439 E | 2/1997 | Rosenberger | 132/321 |
| 5,603,921 A | 2/1997 | Bowen | 424/49 |
| 5,711,935 A | 1/1998 | Hill et al. | 424/49 |
| 5,718,251 A | 2/1998 | Gray et al. | 132/321 |
| 5,755,243 A | 5/1998 | Roberts et al. | 132/321 |
| 5,760,117 A | 6/1998 | Chen | 524/270 |
| 5,765,576 A | 6/1998 | Dolan et al. | 132/321 |
| 5,787,758 A | 8/1998 | Sheldon | 74/490 |
| 5,830,495 A | 11/1998 | Ochs | 424/443 |
| 5,845,652 A | 12/1998 | Tseng et al. | 132/200 |
| 5,848,600 A | 12/1998 | Bacino et al. | 132/321 |
| 5,884,639 A | 3/1999 | Chen | 132/321 |
| 5,911,228 A | 6/1999 | Curtis et al. | 132/321 |
| 5,918,609 A | 7/1999 | Tsao et al. | 132/321 |
| 5,962,572 A | 10/1999 | Chen | 524/474 |
| 5,998,431 A | 12/1999 | Tseng et al. | 514/300 |
| 6,003,525 A | 12/1999 | Katz | 132/321 |
| 6,027,592 A | 2/2000 | Tseng et al. | 156/167 |
| 6,080,481 A | 6/2000 | Ochs et al. | 428/372 |
| 6,083,208 A | 7/2000 | Modak et al. | 604/265 |
| 6,148,830 A | 11/2000 | Chen | 132/321 |
| 6,161,555 A | 12/2000 | Chen | 132/321 |
| 6,303,063 B1 | 10/2001 | Roberts et al. | 264/178 F |
| 6,371,133 B1 * | 4/2002 | Gant | 132/321 |

* cited by examiner

*Primary Examiner*—Todd E. Manahan
(74) *Attorney, Agent, or Firm*—Ernest V. Linek; Banner & Witcoff, Ltd.

(57) ABSTRACT

Molecularly oriented, thermoplastic elastomeric dental tapes extruded with a melt spinning extrusion carried out at draw ratios from between about 4:1 and about 7.5:1 and draw temperatures from between about 80° and 265° C. having: elongation at break of less than about 50%, an elastic limit of less than about 25% and enhanced tape flex-twist index from between about 2.5 and about 5, with the capacity to release substantive, flake-free, saliva soluble coatings during flossing.

18 Claims, 2 Drawing Sheets

MORPHOLOGY OF BLOCK COPOLYMER TPEs

RELATIVE COST AND PERFORMANCE OF TPEs

ELASTOMERIC MONOFILAMENT DENTAL TAPES

CROSS-REFERENCE TO RELATED APPLICATIONS

This application claims priority from copending U.S. Provisional Patent Application Ser. No. 60/281,667, filed Apr. 5, 2001 and application Ser. No. 60/263,220, filed Jan 1, 2001, the disclosure of which is hereby incorporated herein by reference.

BACKGROUND OF THE INVENTION

The present invention relates to innovative interproximal devices, and more particularly, but not exclusively, dental tapes and flosses produced from modified thermoplastic elastomers. These interproximal devices are shred resistant and coatable with proprietary saliva soluble coatings such as described and claimed in co-pending patent application Ser. No. 60/263,220, filed Jan. 22, 2001. These interproximal devices can be further improved according to the disclosure and claims of pending applications Ser. Nos. 09/330,491, filed Jun. 11, 1999 and 09/368,664, filed Aug. 5, 1999.

Monofilament interproximal devices are described and claimed in U.S. Pat. Nos. Re 35,439; 3,800,812; 4,974,615; 5,760,117; 5,433,226; 5,479,952; 5,503,842; 5,755,243; 5,845,652; 5,884,639; 5,918,609; 5,962,572; 5,998,431; 6,003,525; 6,083,208; 6,148,830; 6,161,555; and 6,027,592, the disclosures of which are hereby incorporated herein by reference. These dental tapes generally have serious shortcomings in gentleness, in delivering coatings during flossing and in being handled easily and conveniently during flossing.

Polytetrafluoroethylene (PTFE) based interproximal devices are described in: U.S. Pat. Nos. 5,209,251; 5,033,488; 5,518,012; 5,911,228; 5,220,932; 4,776,358; 5,718,251; 5,848,600; 5,787,758; and 5,765,576. To date, no commercial versions of these tapes have been coated effectively and cannot be used to deliver active ingredients, interproximally and subgingivally during flossing. Handling during flossing is difficult. Most have to be folded to provide a consumer acceptable edge. Many are plagued with serious dimensional inconsistency problems, as well.

Multifilament, interproximal devices are described and claimed in U.S. Pat. Nos. 5,033,365; 3,943,949; 6,080,481; 5,830,495; 2,667,443; 4,638,823; 4,029,113; 2,772,205; 4,627,975; 4,414,990; 3,699,979; 3,897,795; 3,838,702; 4,776,358; 5,718,251; 5,603,921; 5,558,901; 5,423,337; 5,357,990; 4,986,288; 3,897,795; 3,928,618; 5,433,226 and 4,033,365, which are hereby incorporated herein by reference.

The Hill, et al., patents, namely U.S. Pat. Nos. 4,911,927; 5,098,711, 5,165,913; and 5,711,935; describe compression loaded multifilament flosses. All multifilament interproximal devices pose major consumer problems in the areas of shredding, breaking, etc. It is this shortcoming that was the basis for the commercial success of PTFE and other monofilament devices.

All of the foregoing references are relevant and are hereby incorporated by reference. These references fail to teach or suggest the use of the modified thermoplastic elastomeric (or TPE), monofilament materials of the present invention as dental tapes or flosses. Nor does the prior art teach or suggest the substantial consumer advantages these modified TPE tapes offer over current tapes, as well as over multifilament flosses. These advantages are detailed below.

SUMMARY OF THE INVENTION

The present invention relates to modifying thermoplastic elastomer based tapes using molecular orientation to reduce elongation at break below about 50%, along with an elastic limit of less than about 25%. These atypical elastomer properties are attained along with an enhancement of gentleness. These modified TPE dental tapes can be coated with proprietary, substantive, saliva soluble, crystal-free coatings that are totally released during flossing.

This combination of properties makes these modified TPE tapes uniquely qualified as interproximal devices. That is, this modulation of typical elastomer stretching and elastic limit properties allows the modified tape to be coated with substantially crystal-free coatings and to retain these coatings with substantially no flaking during use while releasing substantially all of these coatings into the oral cavity during flossing.

These modified thermoplastic elastomeric tapes release these coatings during flossing while providing a substantive surface for these coatings to adhere to with substantially no flaking. The modified TPE monofilament tapes of the present invention combine the shred resistance and improved interproximal insertion features of monofilament tapes such as the PTFE, bicomponent and homopolymer commercial tapes marketed today, with the "hand", mouth feel and "load" delivery attributes of certain commercial multifilament dental flosses.

The innovative thermoplastic elastomeric tapes of the invention bridge the gap between "tapes and flosses" and, in fact, replace both commercial tapes such as Gore's Glide®, J&J's Easy Slide® and Oral-B's Satin®, along with commercial waxed dental flosses such as J&J's REACH® Waxed Mint Dental Floss.

The broad appeal of these modified thermoplastic elastomeric tapes with saliva soluble coatings to both monofilament tape users and multifilament floss users poses a major advance in interproximal devices that promises to encourage flossing compliance while delivering during flossing a wide range of soft abrasives, cleaners, mouth conditioners, and active ingredients interproximally and subgingivally, with a minimum of shredding and breaking.

Accordingly, the present invention is directed to oriented thermoplastic elastomer based dental tapes extruded with melt spinning extrusions carried out at draw ratios from between about 4:1 and about 7.5:1, and draw temperatures from between about 80° and about 265° C., wherein said oriented tapes have:

an elongation at break of less than about 50%, and an elastic limit of less than about 25%, and where said thermoplastic elastomer is selected from the group consisting of styrenics, olefinic blends, elastomeric alloys, urethanes, copolyesters, polyamides and mixtures and/or copolymers thereof.

Advantageously, the oriented thermoplastic elastomer based dental tapes described herein, have a tape flex-twist index from between about 2.5 and about 5, wherein a processing additive is employed in said melt spinning extrusion.

Advantageously, the processing additive is selected from the group consisting of ultra-high molecular weight polydimethylsiloxanes in organic resin carriers, copolymers, calcium stearate and mixtures thereof.

Advantageously, the organic resin carrier for said processing additive is selected from the group consisting of: polypropylene, polybutylene terephthalate, ethylene maleic acid, high density polyethylene, nylon and mixtures thereof.

Advantageously, the oriented thermoplastic elastomer based dental tapes according to the present invention have:

a. a break strength from between about 10 Newtons and about 40 Newtons, b. a gentleness perception from between about 5 and about 8, c. a Shore D hardness from between about 30 and about 40, and d. a tape flex-twist index from between about 2.5 and about 5.

Advantageously, the thermoplastic elastomer based dental tapes according to the present invention comprise polyamides that are selected from the group of structural formulas consisting of:

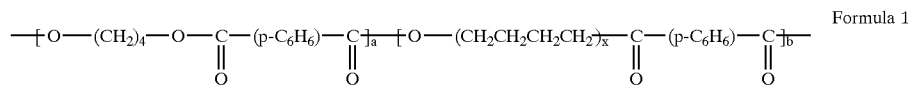
Formula 1 wherein: a=16 to 40, x=10 to 50, and b=16 to 40;

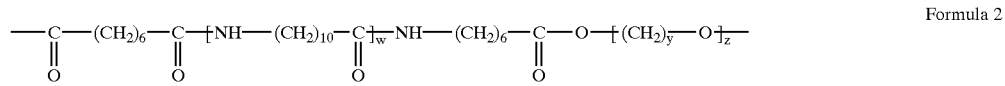
Formula 2

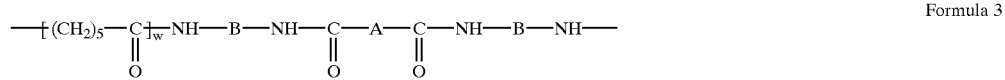
Formula 3

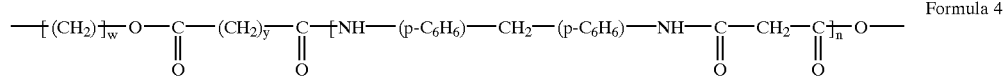
Formula 4 wherein A is a $C_{19}$ to $C_{21}$ dicarboxylic acid and wherein B is:

and wherein n, v, w, y and z are whole numbers; and

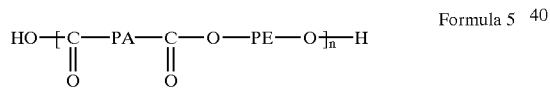
Formula 5 where PA represents the polyamide segment and PE the polyether segment and n is a whole number.

Advantageously, the oriented thermoplastic elastomer based dental tapes according to the present invention comprise a polyamide having the structural Formula 1:

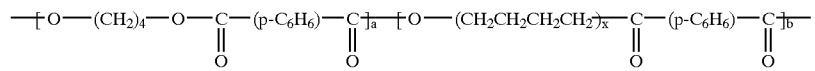

wherein: a and b=16 to 40 and x=16 to 50.

Advantageously, the oriented thermoplastic elastomer based dental tapes according to the present invention comprise a thermoplastic elastomer which is a polyamide having the structural Formula 2:

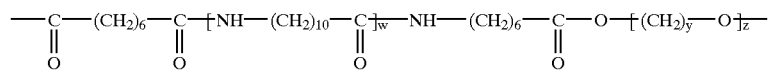

wherein w and z are whole numbers.

Advantageously, the oriented thermoplastic elastomer based dental tapes according to the present invention comprise a thermoplastic elastomer that is a polyamide having the structural Formula 3:

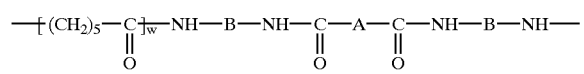

wherein
A=$C_{19}$ to $C_{21}$ dicarboxylic acid and
B=—$(CH_2)_3$—O—[$(CH_2)_4$—O—]$_v$—$(CH_2)_3$—.

Oriented thermoplastic elastomer based dental tapes according to claim 1, wherein said thermoplastic elastomer is a polyamide having the structural Formula 4:

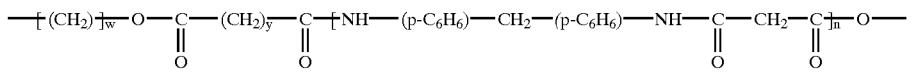

wherein n, y and w are whole numbers.

Advantageously, the thermoplastic elastomer is a polyamide having the structural Formula 5:

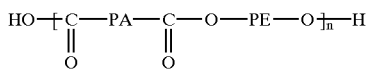

where PA represents the polyamide segment and PE the polyether segment and n is a whole number.

Another embodiment of the present invention is a method for the melt spinning extrusion of oriented thermoplastic elastomer based dental tapes comprising the steps of:
   a. melting said thermoplastic at melt temperatures ranging from between about 170° C. and about 300° C.,
   b. compressing said melt through suitable sized tape-shape holes in a melt spinning extruder,
   c. taking up said tape at a spinning speed while passing said tape through a cooling bath, and
   d. drawing said cooled tape at draw ratios from between about 4:1 and about 7.5:1 at draw temperatures from between about 80° C. and about 265° C.

Advantageously, the method according to the present invention further utilizes a melt spinning extruder wherein said tape-shaped holes are selected from holes having a width from between about 1.05 mm and about 2.15 mm and a thickness from between about 0.05 mm and about 0.09 mm and tapes produced from these holes have a decitex from between about 700 and about 1700.

Advantageously the oriented thermoplastic elastomer based dental tapes according to the present invention have an elastic limit up to about 15%.

Advantageously the oriented thermoplastic elastomer based dental tapes according to present invention have a tape flex-twist index from between about 2.5 and about 5.

Advantageously the oriented thermoplastic elastomer based dental tapes according to the present invention may be coated with substantive, saliva soluble, crystal-free coatings that are substantially flake-free, wherein said coatings are substantially totally released interproximally and subgingivally during flossing.

Advantageously, the oriented thermoplastic elastomer based dental tapes according to the present invention may be used to deliver substantive, flake-free, saliva soluble coatings to interproximal and subgingival sites during flossing.

Advantageously, the oriented thermoplastic elastomer based dental tapes according to the present invention may be coated with substantive, crystal-free coatings having Shore D hardness substantially lower than commercial dental tapes.

Another embodiment of the present invention comprises a method of treating interproximal and subgingival areas in the oral cavity comprising flossing said areas with an oriented thermoplastic based dental tape having an elongation at break of less than about 50% and an elastic limit up to 25%, wherein said tape is coated with substantive, crystal-free coatings that are substantially flake-free and totally released from said tape during flossing.

Another embodiment of the present invention comprises providing an oriented thermoplastic elastomer based dental tape having a color throughout selected from the group consisting of green, blue, aqua, orange and purple.

BRIEF DESCRIPTION OF THE DRAWINGS

The modified thermoplastic elastomer based dental tapes of the present invention are described further in FIGS. 1, 2 and 3.

As to FIG. 1, the morphology of block polymer thermoplastic elastomers suitable for the dental tapes of the present invention is illustrated, where A depicts the hard thermoplastic domain of the block copolymer under molten conditions and B depicts the soft elastomeric domain of the block copolymers under solidified conditions.

Figure 2:
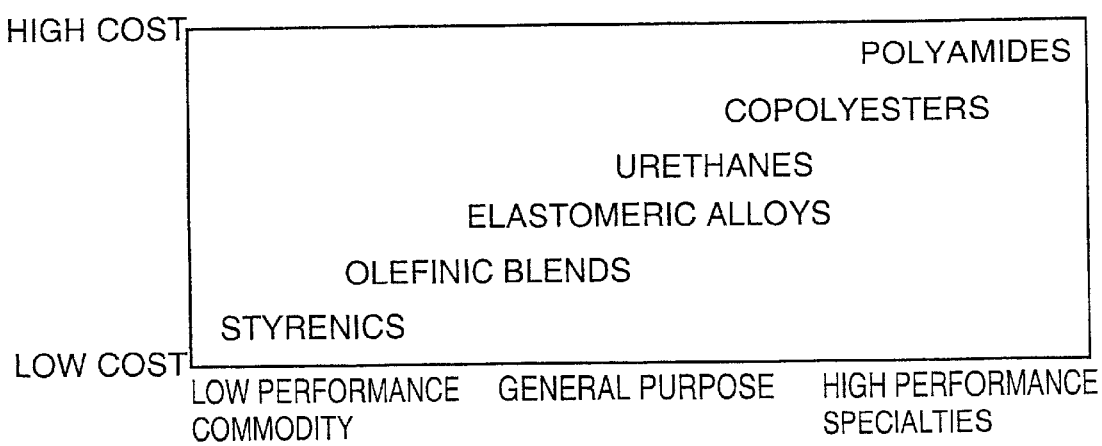

As to FIG. 2, the relative costs of the six classes of modifiable thermoplastic elastomers are compared against the level of performance.

Figure 3:
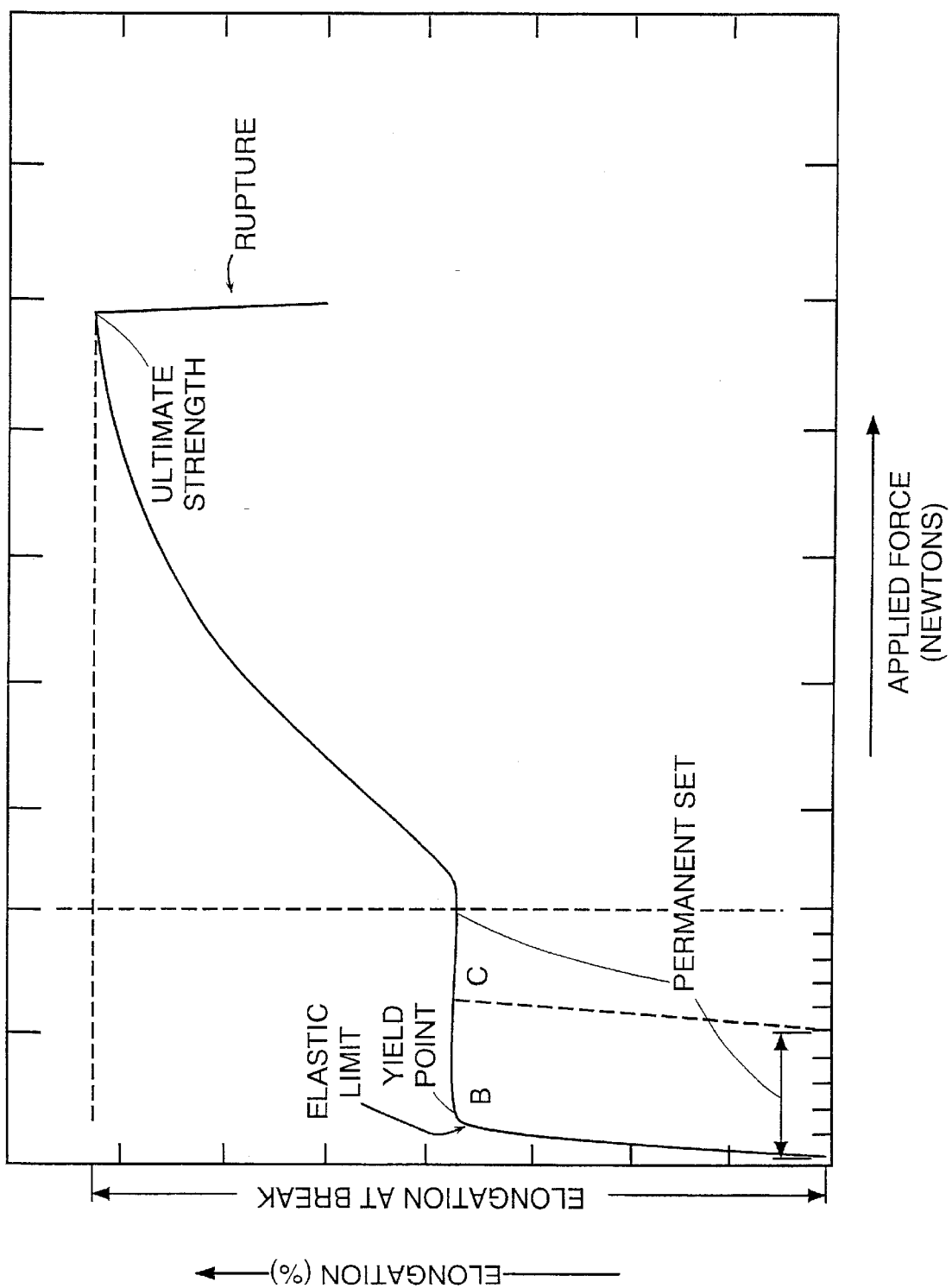

As to FIG. 3, a plot is shown of applied force versus elongation for a wide variety of materials. At low applied force (such as would be applied by pulling the dental tape of this invention wrapped around the fingers), the material elongates easily until the Elastic Limit is reached. Then additional force must be applied with no appreciable elongation until the point of permanent set is reached and elongation with permanent deformation is introduced. At the point of ultimate strength (Break Strength in Newtons in the Examples given for this invention) the tape ruptures and the stress is relieved.

KEY DEFINITIONS

For the purposes of the present invention, key technical terms including: melt temperature, draw temperature, draw ratio, break strength, decitex, elongation to break and Shore D hardness have accepted definitions as set forth in the prior art, whereas the terms: gentleness perception, tape flex-twist index and elastic limit are defined for purposes of the present invention as set forth in the introduction to Tables 4 to 7 below.

PREFERRED ASPECTS OF THE INVENTION

According to one preferred aspect of this invention, there is provided an interproximal device formed from a thermoplastic elastomer by extrusion carried out at a draw ratio of between about 4:1 and about 7.5:1, and a draw temperature of between about 80° C. and about 265° C., wherein said oriented device has:
   an elongation at break of less than about 50%, and
   an elastic limit of less than about 23%,
where said thermoplastic elastomer is selected from the group consisting of styrenics, olefinic blends, elastomeric alloys, urethanes, copolyesters, polyamides and mixtures and/or copolymers thereof.

According to another preferred aspect of this invention there is provided an oriented thermoplastic elastomer based interproximal device extruded with melt spinning extrusion carried out at a draw ratio of between about 4:1 and about 7.5:1, and a draw temperature of between about 80° and about 265° C., wherein said oriented device has:
   an elongation at break of less than about 50%, and
   an elastic limit of less than about 25%,
where said thermoplastic elastomer Is selected from the group consisting of styrenics, olefinic blends, elastomeric alloys, urethanes, copolyesters, polyamides and mixtures and/or copolymers thereof.

According to another aspect of this invention there is provided a molecularly oriented, thermoplastic elastomeric interproximal device extruded with a melt spinning extrusion carried out at a draw ratio of between about 4:1 and about 7.5:1 and a draw temperature of between about 80° and 265° C. having elongation at break of less than about 50%, an elastic limit of less than about 25% and enhanced tape flex-twist Index from between about 2.5 and about 5 with the capacity to release substantive, flake-free, saliva soluble coatings during flossing.

According to preferred another aspect of this invention there is provided a method for the extrusion of a thermoplastic elastomer based interproximal device comprising:

a. melting said thermoplastic at a melt temperature in a range of between about 170° C. and about 300° C., b. compressing said melt through suitable sized and shaped holes in an extruder, c. taking up said device while passing said device through a cooling bath, and d. drawing said cooled device at draw ratios from between about 4:1 and about 7.5:1 at a draw temperature in a range of between about 80° C. and about 265° C.

The extruder may comprise an extrusion die or spinneret.

According to another preferred aspect of this invention there is provided a method for the melt spinning extrusion of oriented thermoplastic elastomer based interproximal device comprising:

a. melting said thermoplastic at a melt temperature in a range of between about 170° C. and about 300° C., b. compressing said melt through suitable sized and shaped holes in a melt spinning extruder, c. taking up said device at a spinning speed while passing said device through a cooling bath, and d. drawing said cooled device at a draw ratio of between about 4:1 and about 7.5:1 at a draw temperature in a range of between about 80° C. and about 265° C.

An especially preferred embodiment of the interproximal device described in the preceding five paragraphs is a dental interproximal device which may be in the form of a dental tape or floss.

The especially preferred embodiments of the present invention concern dental tapes or flosses produced from modified thermoplastic elastomers. These tapes or flosses are shred resistant and coatable with proprietary saliva soluble coatings such as described and claimed in co-pending U.S. patent application entitled "Improved Dental Tape" filed on Jan. 22, 2001.

The especially preferred embodiments of the present invention concern modifying thermoplastic elastomer (TPE) based tapes using molecular orientation to reduce elongation at break below about 50%, along with an elastic limit of less than about 25%. These atypical elastomer properties are attained in the preferred embodiments along with an enhancement of break strength and gentleness. These modified TPE dental tapes can be coated with proprietary, substantive, saliva soluble, crystal-free coatings that are totally released during flossing.

This combination of properties makes these modified TPE tapes of the especially preferred embodiments uniquely qualified as interproximal devices. That is, this modulation of typical elastomer stretching and elastic limit properties allows the modified tape to be coated with substantially crystal-free coatings and to retain these coatings with substantially no flaking during use while releasing substantially all of these coatings into the oral cavity during flossing.

These modified thermoplastic elastomeric tapes of the especially preferred embodiments release these coatings during flossing while providing a substantive surface for these coatings to adhere to with substantially no flaking. The modified TPE monofilament tapes of the preferred embodiments combine the shred resistance and improved interproximal insertion features of monofilament tapes, such as the PTFE, bicomponent and homopolymer commercial tapes marketed today, with the "hand", mouth feel and "load" delivery attributes of certain commercial multifilament dental flosses.

Another preferred aspect of the invention is to develop a modified thermoplastic elastomer based dental tape with elongation at break of less than about 50% and an elastic limit up to 25%, i.e., the propensity after stretching not to return to pre-stretching dimensions.

Another preferred aspect of the invention is to develop modified thermoplastic elastomer based dental tapes that can be coated with substantive crystal-free coatings that are substantially flake free.

Still another preferred aspect of the invention is to develop modified thermoplastic elastomer based tapes with enhanced tenacity and gentleness suitable for use as dental tape to deliver saliva soluble coatings interproximally and subgingivally during flossing.

Yet another preferred aspect of the invention is to develop a modified thermoplastic elastomeric based dental tape from a wide range of thermoplastic elastomers including styrenics, olefinic blends, elastomeric alloys, urethanes, copolyesters and polyamides.

A further preferred aspect of the invention is to provide a method for manufacturing modified thermoplastic elastomer based dental tapes having improved tenacity and gentleness and elongation at break of less than about 50%, along with an elastic limit up to 25%.

Another preferred aspect of the invention is to provide a means for treating, cleaning and/or flossing interproximal and subgingival sites with a modified thermoplastic elastomer based dental tape coated with a saliva soluble coating that is released during use.

Still another preferred aspect of the invention is to provide modified thermoplastic elastomer based dental tapes that provide superior consumer attributes over monofilament tapes and multifilament dental flosses.

Yet another preferred aspect of the invention is to provide lower cost, superior monofilament tapes suitable for coating with substantive, crystal-free, totally saliva soluble, flake-free coatings.

A final preferred aspect of the invention is to improve flossing compliance among non-flossers with modified thermoplastic elastomer based dental tapes coated with substantive, crystal-free, saliva soluble coatings.

DETAILED DESCRIPTION OF THE PREFERRED EMBODIMENTS

The tapes of the present invention are extruded from thermoplastic elastomers (TPEs). Thermoplastic elastomers are a diverse family of rubber-like materials that, unlike conventional vulcanized rubbers, can be processed and recycled like thermoplastic materials. In terms of properties and functional use, TPEs are a rubber. In terms of processing and fabrication, TPEs are thermoplastic.

The birth of TPEs occurred in the 1950s with the development of the thermoplastic polyurethanes (TPUs). These were the first true commercial TPEs, evolving from the discovery of polyurethanes in the 1930. Heavily plasticized polyvinyl chloride (PVC) was commercialized by B. F. Goodrich Company just before World War II and has many desirable rubber-like properties but does not meet the accepted definition of a rubber.

In the early 1960s, Shell Development Company introduced another class of TPEs, the styrene-diene block copolymers, to the industrial market. These were followed in the 1970s by copolyester (COP) TPEs from duPont de Nemours & Company and thermoplastic polyolefin-elastomer blends, known as TPOs, from Uniroyal. Blends of PVC and nitrile rubber (NBR) with some elastomeric properties and thermoplastic processability were also developed during this period, but these have had more significance in Japan than in North America and Europe. Elastomeric alloys (EAs), now called thermoplastic vulcanizates) were commercialized in 1981 by Monsanto Chemical Company, based on compositions of thermoplastic and crosslinked rubber. TPEs with the highest performance and highest cost, the elastomeric polyamides (PEBAs), were introduced in the early 1980s.

Virtually all TPEs consist of at least two polymeric phases: a hard thermoplastic phase and a soft elastomeric phase. The properties of the resulting TPE will be derived from the properties of each of the two phases and their mutual interaction. The two phases may result from simply mixing two different polymers, as in a blend of a hard thermoplastic such as polypropylene (PP) with a soft elastomer such as ethylene-propylene terpolymer (EPDM rubber), to give a thermoplastic elastomeric olefin (TEO). Dynamic vulcanization (under conditions of high shear and temperature) of the elastomer phase of such a blend gives use to a thermoplastic vulcanizate (TPV), with properties much closer to those of a conventional thermoset rubber. The two phases of a TPE may also be present as alternating hard and soft segments along a common polymer backbone. This is the case for block copolymers, the basis for many commercially important TPEs. Table 1 compares the performance characteristics of six different generic classes of TPEs.

Various TPEs suitable for the purposes of the present invention are described in the following U.S. Pat. Nos. 5,086,121; 4,311,628; 5,354,811; 5,070,111; 5,244,978; as well as the corresponding patents covering the various commercial TPEs described in Table 4 below, all of which are hereby incorporated by reference.

The performance characteristics of a TPE depend on the melting point ($T_m$) of the hard thermoplastic phase and the glass-transition temperature ($T_g$) of the soft elastomeric phase. The useful temperature range for a TPE is between $T_m$ and $T_g$. Within this range, the hard thermoplastic phase melts, and the TPE becomes fluid and can be processed by usual thermoplastic techniques. Below $T_g$ the TPE becomes brittle and loses all of its useful elastomeric characteristics.

Block copolymer TPEs contain both hard and soft segments along a common polymer chain as illustrated below. See also FIG. 1. At temperatures below the effective $T_m$ of the hard phase, the hard segments will aggregate into rigid domains, making the TPE a solid. At these temperatures, the soft segments are present as amorphous rubbery domains that impart at least some elastomeric nature to the TPE. In the useful service temperature region of a block copolymer TPE, the hard phase will restrict the motion of the soft phase segments in much the same way as the crosslinks of a thermoset rubber restrict the motion of the elastomer chains. TPE block copolymers include polymers of styrenes and dienes (the styrenics), copolyesters, polyurethanes and polyether block amides.

Of the 6 classes of elastomers useful for the purposes of the present invention, the copolyesters and the polyamides are particularly preferred for the tapes of the present invention.

TABLE 1

Key Properties of Generic Classes of TPEs*

| Property | Styrenic | TEO | TPV | Copolyester | Polyurethane | Polyamide |
|---|---|---|---|---|---|---|
| Specific gravity† | 0.90–1.20 | 0.89–1.00 | 0.94–1.00 | 1.10–1.40 | 1.10–1.30 | 1.00–1.20 |
| Shore hardness | 20A–60D | 60A–65D | 35A–50D | 35D–72D | 60A–55D | 60A–65D |
| Low temperature limit, ° C. | −70 | −60 | −60 | −65 | −50 | −40 |
| High temperature limit ° C. (continuous) | 100 | 100 | 135 | 125 | 120 | 170 |
| Compression at resistance, at 100° C. | P | P | G/E | F | F/G | F/G |
| Resistance to aqueous fluids | G/E | G/E | G/E | F | F/G | F/G |
| Resistance to hydrocarbon fluids | P | P | F/E | G/E | F/E | G/E |

* P = Poor; F = Fair; G = Good; E = Excellent
† Does not include grades containing a special flame-retardant package, which generally raises the specific gravity 20 to 30 percent Polymers with the -A-B-A-B structure, where A and B are alternating hard and soft polymeric segments connected by ester linkages are known as copolyesters, COPs. These are illustrated in the structural formula below:

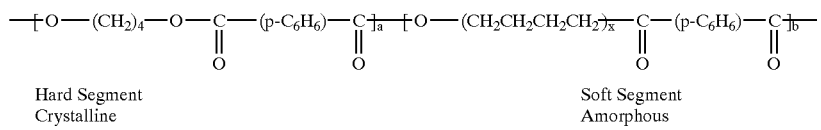

Hard Segment         Soft Segment
Crystalline          Amorphous wherein: a=16 to 40, x=10 to 50, and b=16 to 40.

These block copolymers differ from simple polyester thermoplastics, which are typically hard crystalline polymers of organic dibasic acids and diols. As shown in FIG. 2, COPs offer an excellent combination of properties and are accordingly priced higher than TEOs or TPVs.

Figure 1:
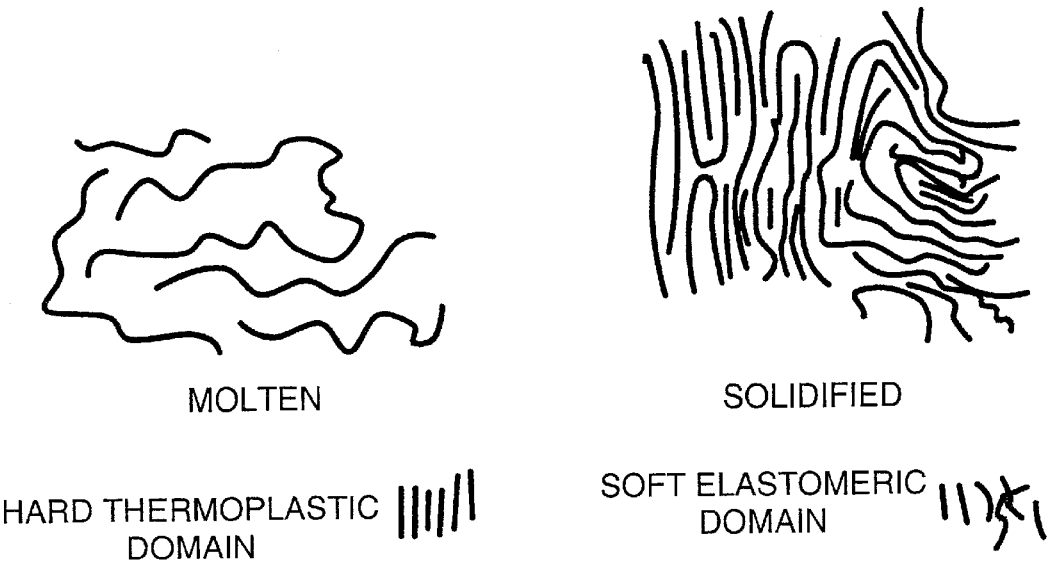

The morphology of COPs is that shown in FIG. 1. These materials perform as TPEs if the structures of A and B are chosen to give rubbery properties to the copolymer over a useful temperature range. The glass transition point of the soft segment defines $T_g$ for the COP and should be low enough to prevent brittleness at the lowest temperature to which the working material will be exposed. The structure of this segment provides the flexibility and mobility needed for elastomeric performance. The melting point of the hard segment should be high enough to allow the material to maintain a fabricated shape at the highest temperature experienced, but low enough to allow processing on standard thermoplastics equipment. The necessary characteristics for a soft segment are provided by polyether linkages such as illustrated in the structural formula set out above.

Preferred TPEs for use in the dental tapes of the present invention are the polyether block amides, PEBAs, as well as polyether/ester TPE. The block copolymeric PEBAs have amide linkages that connect the hard and soft segments of these TPEs while the soft segment may have a polyester or polyether structure similar to the COPs. The structural formulas for three typical commercial PEBAs are set out below:

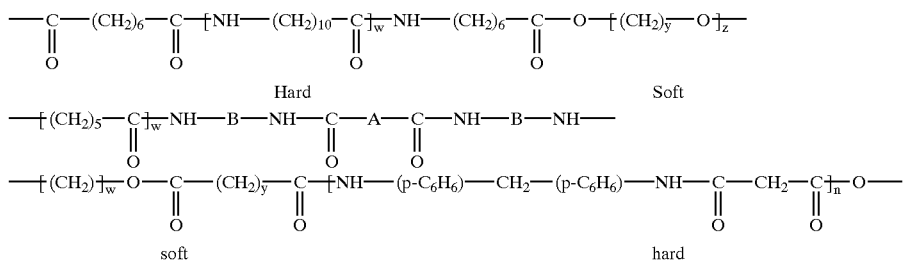

wherein A is a $C_{19}$ to $C_{21}$ dicarboxylic acid and B is:

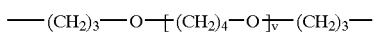

and wherein n, v, w, y and z are whole numbers and wherein.

The morphology of PEBAs is that of the typical block copolymers as shown in FIG. 1.

The amide linkages connecting the hard and soft blocks of PEBAs are more resistant to chemical attack than either an ester or a urethane bond. For this reason, PEBAs typically have higher temperature and chemical resistance than TPUs or COPs, and, as a result, their cost is greater.

The structure of the hard and soft blocks also contributes to the performance characteristics of PEBAs. The soft segments may consist of polyester, polyether, or polyether-ester chains. Polyether chains give better low-temperature properties and resistance to hydrolysis, while polyester chains in the soft segment give better fluid resistance and resistance to oxidation at elevated temperatures. As in other block copolymer TPEs, the nature of the hard segments determines the melting point of the PEBAs and their performance at elevated temperatures.

PEBAs cover a wide hardness range, from a high of 72 Shore D down to 60 Shore A and can therefore be softer than COPs but not as soft as some TPUs. These elastomeric PEBAs have useful tensile properties at ambient temperatures and excellent retention of these properties at higher temperatures. A 50 Shore A PEBA retains more than 50 percent of its tensile strength and modulus at 100° C. Annealing a PEBA above the melting point of the hard phase can result in significant increases in tensile strength, modulus, and ultimate elongation. PEBAs are second only to TPUs in abrasion resistance, and show excellent fatigue resistance and tear strength, which is ideal for use as a dental tape.

Another preferred PEBA for purposes of the present invention is ELF ATOCHEM's PEBAX® polyether block amides. The PEBAX® structure consists of a regular linear chain of rigid polyamide segments interspaced with flexible polyether segments. PEBAX® have the general chemical formula:

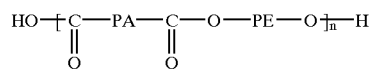

where PA represents the polyamide segment and PE the polyether segment and n is a whole number.

An analysis of the macromolecular chain arrangement in the solid state shows a morphological structure is similar to that illustrated in FIG. 1 with an amorphous/molten phase and a solidified crystalline phase.

PEBAX® polyether block amides are plasticizer-free, thermoplastic elastomers featuring outstanding mechanical, physical and chemical properties over a wide flexibility range.

PEBAX® Polyether Block Amides bridge the gap between thermoplastics and rubbers in shore hardness with various PEBAX® grades having shore hardness between 70A and 72D, based on Standard ASTM 2240.

PEBAX® can be extruded using the same types of machines and screws as used for polyamide extrusion.

The PEBAX® 33 series resins are particularly preferred for extruding the dental tapes of the present invention. Key property comparisons of the PEBAX® 33 resins are set out in Table 2.

TABLE 2

PEBAX ® Resin Grades

| Property | ASTM TEST METHOD | UNITS | 7233 | 7033 | 6333 | 5533 | 4033 | 3533 | 2533 |
|---|---|---|---|---|---|---|---|---|---|
| Specific Gravity | D792 | | 1.02 | 1.02 | 1.01 | 1.01 | 1.01 | 1.01 | 1.01 |
| Water Absorption | D570 | % | — | 0.64 | — | 0.5 | 0.5 | 0.5 | 0.5 |
| Equilibrium 20° C., 50% RH>) | | | — | 0.83 | — | 1.2 | 1.2 | 1.2 | 1.2 |
| 24 Hr. Immersion | | | | | | | | | |
| Hardness | D2240 | Shore | 72D | 69D | 63D | 55D | 40D | 35D | 25D |
| Tensile Strength, Ultimate | D638 | psi | 9210 | 8300 | 8100 | 7300 | 5700 | 5600 | 4950 |
| Elongation, Ultimate | D638 | % | 360 | 400 | 300 | 430 | 390 | 580 | 640 |
| Flexural Modulus | D790 | psi | 107000 | 67000 | 49000 | 29000 | 13000 | 2800 | 2100 |
| Izod Impact, Notched 20° C. −40° C. | D256 | ft-lb/in. | 1.4 1.4 | NB 0.95 | NB 1.5 | NB NB | NB NB | NB NB | NB NB |
| Abrasion Resistance H18/1000 g | D1044 | Mg/1000 Cycles | 29 | 57 | 84 | 93 | 94 | 104 | 161 |
| Tear Resistance Notched | D624C | lb/in. | 1400 | 900 | 850 | 650 | 400 | 260 | 220 |
| Melting Point | D3418 | ° F. | 348 | 345 | 342 | 334 | 334 | 306 | 298 |
| Vicat Softening Point | D1525 | ° F. | 327 | 329 | 322 | 291 | 270 | 165 | 140 |
| HDT 66 psi | D648 | ° F. | 223 | 208 | 194 | 151 | 126 | 115 | 108 |
| Compression Set (24 hr., 160° F.) | D395A | % | — | 6 | 6 | 10 | 21 | 54 | 62 |

Other preferred thermoplastic elastomers suitable for modification include thermoplastic olefin (TPO) blends, styrene-block TPEs with plasticized polyvinylchloride (PVC) in select locations. For example, Vistaflex® elastomer is a TPO with an unvulcanized rubber phase. Particularly preferred Vistaflex®) elastomers include Vistaflex® 641-N and Vistaflex® 671-N.

The TPEs described in Examples 27–32 in Table 5 offer some of the most promising, break strength tapes with elastic limits and preferred utility factors.

The modified thermoplastic elastomer tapes of the present invention are manufactured using a fiber melt spinning extrusion process. In this process, the thermoplastic elastomer melt is shaped into a tape by forcing it to flow through a small orifice and pulling it away from the orifice by a take-up device at a speed defined as the spinning speed, which is higher than that at the exit of the orifice.

TPE tapes particularly useful as dental tapes are produced from a die with a series of holes that can be cut to a range of dimensions. For example, suitable sized holes include: 6 mm×0.4 mm; 8 mm×0.25 mm; 5 mm×0.375 mm; 12 mm×0.325 mm and various combinations thereof. In a particularly preferred embodiment of the invention, the die has twelve (12) holes, each cut to the following dimensions: 8 mm×0.325 mm. The extruder fitted with this die produces twelve tape ends simultaneously.

Preferably, between the exit of each hole and the take-up device each of the drawing-down spin lines is cooled by passing through a water bath. Subsequently, these spun tapes are further oriented by drawing in the solid state to impart the unique and unexpected properties discussed above, which make these tapes particularly effective as dental devices.

This orientation substantially reduces the elongation and imparts elastic limits to the TPE modified tapes of the present invention. Elongations of 50% or less are quite common with elongations from between about 20% and about 40% preferred (see Tables 4–7 below). The most unexpected feature of the oriented thermoplastic elastomer is the propensity not to return to the original dimension after stretching, i.e., elastic limit (see Tables 4–7 below, and FIG. 3). This reduced elongation, in combination with resistance to return to original dimension after stretching, provides the means for coating saliva soluble coatings that do not flake off, while delivering the hand, gentleness, tenacity and resistance to shredding properties which are so essential to effective interproximal device performance.

Melt spinning with corresponding fiber structure formation was first described in 1932, and the first successful commercial melt spinning process was that of Nylon 66 in 1939. However, the first quantitative description of the dynamics of the spinline and the rheological and structural formation phenomena occurring along the spinline appeared in a series of papers published in 1959–1962. Since then, several studies have been published on the mechanics of steady-state fiber spinning, on threadline stability, on structure development along the spinline, and on the effect of spinning conditions on the properties of the spun fibers. All of these teachings are hereby incorporated by reference.

It has been further unexpectedly found that when certain processing additives as described in detail below are used in the melt spinning process of the present invention, the thermoplastic elastomer molecules can be more effectively modified, i.e., oriented, to produce the low elongation, "no-return-to-original-dimensions-after-stretching" properties that are so critical to the performance of these thermoplastic elastomer based tapes as interproximal devices.

These processing additives useful for the extrusion process of the present invention help increase processing speeds, elastomer flow, reduce energy consumption, processing temperatures and pressure. As to the finished product certain of these processing aids also enhance the tape's mechanical properties, reduce surface defects and melt fracture. In addition, certain of the silicone additives improve: lubricity, slip, abrasion resistance, while lowering the co-efficient of friction. All of these product enhancements contribute substantially to the performance of the modified TPE tapes of the present invention.

These processing additives are usually used at levels between about 0.6% and about 1.0% with levels as high as 5% sometimes used for enhancing specific tape properties. See Tables 4–7 below.

Processing aids are added to TPEs to enhance fusion and melt properties. These processing aids are typically very high molecular weight polydimethyl-siloxane polymers and are used at low levels in the dry blend. They function by increasing the frictional forces between the TPE, and the internal metal surface of melt mixing equipment to enhance TPE fusion. The high molecular weights of these processing additives are also effective in helping to control melt viscosity.

These processing additives are usually incorporated into the spinning process as pellets, which are mixed with the elastomer pellets. However, there are instances that free flowing powders of these processing additives may be more desirable than the pellet form.

The commercial processing ultra-high molecular weight polydimethyl-siloxane additives suitable for use in the present invention are generally combined with an organic resin carrier, such as high density polyethylene, high-impact polystyrene, thermoplastic polyester elastomer and polypropylene thermoplastic with epoxy reactivity, thermoplastic with methacrylate reactivity and thermoplastic with amine reactivity. These processing additives are available commercially from Dow Corning Corp., Midland, Mich. 48686-0994, under the trade names Dow Corning: MB50-002 (Silicone dispersed in polyethylene) MB50-004 (Silicone dispersed in high-impact polystyrene), MB50-010 (Silicone dispersed in Hytrel polyester elastomer), MB50-001 (Silicone dispersed in polypropylene), 4-7105 Resin Modifier, 4-7051 Resin Modifier, 4-7081 Resin Modifier, 1-9641 Resin Modifier. See Tables 4–7.

Examples of other processing additives suitable for the dental tapes of the present invention include fluorinated copolymers such as ATOFINA's Kynar Flex PPA, and polydimethylsiloxanes without resin carriers including PDMS materials with molecular weights from several hundred thousand up to 50 million cs.

The influence of processing aids such as calcium stearate on the orienting process for the thermoplastic elastomeric tapes of the invention is clearly established in some of the examples in Tables 4–7 below.

Most dental tapes are marketed as a white tape. Accordingly, a "whitening load" of $TiO_2$ is preferably added to the extrusion process. For example, the tapes described in Tables 4–7 each contain 3% $TiO_2$. Of course, other color ingredients could be added as required. For example, pigments to produce blue, green and aqua tape would be suitable with green tape suggesting "mint" flavor and blue tape suggesting cleaning. Various decorated and physically modified tapes suitable for the present invention are described in the following co-pending provisional patent applications:

| U.S.S.N | Title | Filing Date |
|---|---|---|
| 60/227,196 | Self-Indicating Dental Tape | 23 Aug. 2000 |
| 60/227,239 | Gentle-Edge Dental Tape | 23 Aug. 2000 |
| 60/227,240 | Visually Striped Dental Tapes | 23 Aug. 2000 |
| 60/227,244 | Chemotherapeutic Dental Tapes | 23 Aug. 2000 |
| 60/227,255 | Water-Insoluble, Inverse Emulsion | 23 Aug. 2000 |
| 60/227,433 | Water-Soluble Coatings for Tapes | 23 Aug. 2000 |
| 60/227,246 | Feather-Edged Dental Tapes | 23 Aug. 2000 |

These provisional applications are hereby incorporated by reference.

The enhanced softness of the TPE tapes of the present invention is key to the tapes consumer perception of gentleness, which is a distinct advantage over current commercial monofilament tapes and multifilament waxed flosses.

Tables 4–7 below describe in detail various modified TPE tapes of the present invention. The "UTILITY FACTORS": Gentleness Perception, Tape Flex-Twist Index and Hardness Shore D, all contribute to the consumer perception of gentleness.

Wound bobbins of the tape of the present invention showed substantially lower Shore D hardness values than competitive tapes when tested with the Flexbar Portable Shore Hardness Tester Model Number 18877. See Table 3 below. This aspect of gentleness, of course, is primarily attributed to the substantive, saliva soluble, flake-free coating applied to the modified TPE tapes of the invention.

TABLE 3

| Bobbin Type | Polymer Type | Tape Coating | Shore D Hardness |
|---|---|---|---|
| Glide ® Floss-mint | PTFE | Wax | 36 |
| Glide ® Tape | PTFE | Wax | 36 |
| Oral-B ® Satin ® Tape-mint | Bicomponent | Wax | 29 |
| Fibaclean ™ unwaxed | PEBA | None | 37 |
| Fibaclean ™ noncrystalline coating | PEBA | Noncrystalline Non flaking | 27 |

The modification of thermoplastic elastomeric tapes to reduce elongation and elastic limit values, i.e. the propensity of the tape not to return to the dimensions before stretching, is unique to the thermoplastic elastomers of the present invention. The only teaching in the art of modulating the properties of these classes of thermoplastic elastomeric tapes is a "cross-linking" process, where cross-linking monomers are activated to impart reduced elasticity to the thermoplastic elastomers. See *MDDI Magazine,* June 1999 article, "Cross-linking thermoplastic elastomers for improved product performance" by L. A. Acquarulo, Jr. and C. J. O'Neil. See also duPont Tetrathane PTMEG Butanediol Technical Information, p. 11.

The invention is further described and illustrated by the various examples set forth below:

EXAMPLE 1

A modified thermoplastic elastomer based dental tape, suitable for the present invention is produced as follows:

PEBA granules (PEBAX® 5033 pellets) are dried and fed into an extrusion hopper. In another hopper, a tumble blended masterbatch of Titanium Dioxide ($TiO_2$) (plus PEBA carrier) and processing aid Dow Corning MB-50-001 ultra-high molecular weight silicone (PDMS) dispersed in polypropylene (PP)

The ratio of PEBA and Masterbatch are:
  90% PEBA
  10% Masterbatch (broken down to 20% $TiO_2$/PP and 80% PDMS/PP)

(The white Master is 60% TiO$_2$: 40%PP and the silicone is 50:50.)

The parameters used in production are as follows (with the processing ranges shown in brackets.)

In the extruder, the following processing conditions are followed:

Feed Zone: 220° C. (200°–230°)
Compression (Mid) Zone: 260° C. (240°–280°)
Metering Zone: 260° C. (240°–280°)
Filter Zone: 260° C. (240°–280°)
Pump Zone: 260° C. (240°–280°)
Die Zone 1: 270° C. (250°–285°)
Die Zone 2: 270° C. (250°–285°)
Die Zone 3: 270° C. (250°–285°)

Pressures at 3 points are controlled:

Pre-filter: 1200 psi (1000–1400)
Pre-pump: 1200 psi (1000–1400)
Die Head: 200 psi (100–300)
Metering Pump: 9.3 rpm (8–11)

The extruder produces 12 PEBA tapes from a die with holes cut to 8 mm×0.375 mm.

From the extruder, the tapes are introduced into a water bath for cooling: The water lies 5–10 mm vertically from the die, and is kept at 19–21° C. The 12 ends on the tape are then fed under a guide bar, then up at an angle of 450 to a water removal fan bar. A second water removal bar is vertically above this, allowing the extrudate to form an 'S' shape.

The pulling action required to take the extrudate through the water bath and water removal bars is achieved by a set of initial haul-off rollers. This is a set of 5 rollers (3 on top, two below), in which the final two rollers the ends pass through are heated.

Roller haul-off setting: 15.3 meters per minute (14–16)
Heated Rollers (both): 100°–110° C. (95°–120°)

After cooling, the tapes are drawn as follows:

The ends are drawn over a hot plate with a speed increase, controlled by a second set of 5 rollers.

Hot plate temperature: 1300 (120°–140°)
Roller Speed: 103 meters per minute (95–110)

These rollers are not actively heated or cooled.

After drawing, there is a 'relaxation stage' where a little stretchability is allowed back into the material, in addition to "setting" the final characteristics. Once again, a 5-roller set-up as described above is used to pull the ends over a hot plate. This set of rollers are chilled, by circulating water through a chiller.

Hot plate temperature: 130° C. (120°–140°)
Roller Speed: 100 meters per minute (92–107)
Circulating Water temperature: 18° C. (16°–20°)

The ends are then wound onto phenolic cones, which have independent tension and torque control, which is adjusted to conditions.

The final product specifications for this run were:

Width: 1.3 mm±0.1 mm
Thickness: 0.060 mm±0.01 mm
Decitex: 650–800
Tenacity: >25N
Elongation: 25–40%

The final product was then coated with a crystal-free, substantially flake-free, saliva soluble coating as described and claimed in co-pending patent application, Ser. No. 60/263,220, using the coating process as described and claimed in said co-pending provisional patent application.

Finished coated versions of this tape were then consumer tested in a sequential, monadic, home placement test against uncoated tape and Glide®. The coated modified TPE tape of the present invention was preferred over the other tapes on each of 11 key consumer attributes.

EXAMPLES 2 THROUGH 59

Various TPEs suitable for purposes of the present invention are set forth in Tables 4 to 7 below. All percentages are percentages by weight. The elongation to break, tenacity and elastic limit values set forth, along with the utility factors as detailed, clearly describe the unexpected and unique features of the dental tapes of the present invention.

Introduction to Tables 4 to 7

Definitions Relating to Tape Composition

"Thermoplastic Elastomer Type" defines the starting material for this invention, not the properties of the invention as practiced. These elastomers, by definition and original intent, are "rubbery" and have the property of being easily stretched or compressed over 100% and often 200–300%. Then, when released, are able to return to their original dimensions over and over. Such properties are useful for "rubber band" effects, sporting goods, shock absorbers, stretchable films, stretchable clothing and hosiery, etc. In the course of exercising this invention, the molecules of the Thermoplastic Elastomer are so oriented that the stretch and return properties are greatly reduced and in some examples the "Elastic Limit" is effectively reduced to zero. By the end of the process and chemistry of the invention, the material no longer possesses the typical properties of an elastomer, but has assumed new, novel and quite surprising properties which make it suitable for use as a tape for dental flossing as described herein. The dental tapes of this invention are thus called "modified thermoplastic elastomers" since they no longer have the expected properties of stretch or compression with return.

"Silicone Process Aid" describes ultra high molecular weight polydimethylsiloxanes and related silicones. In the examples and illustrative examples two methods for incorporating the silicones were employed:

(a) Master batch materials in which the silicones were pre-compounded into another polymer (typically at 50% silicone concentrations) such as polypropylene, or a polymer essentially identical to one part of the Thermoplastic elastomer starting material (e.g., a polyamide like nylon for use with the copolyester/polyamides), (b) the starting TPE itself, and (c) pure silicones in pelletized or powder form.

The tables clearly illustrate when another polymer than the TPE is used in the Master batch by including the appropriate amount of the carrier polymer in the "Secondary Polymer Added" column. Where silicone process aids were introduced either as pure silicone or pre-compounded into the TPE, there is no entry in the Secondary Polymer column as the chemistry effect is identical and the choice is one of operator convenience.

Since TiO$_2$ is very finely divided, it must be added as a Master batch. Thus, when used in an Example, the equivalent amount of carrier polymer is also included in the Secondary Polymer column.

"Secondary Polymers" are included for the purposes mentioned in notes (2) and (3) above. They are also included for further modifying the TPE to achieve certain desired properties of the invention. The examples of EMA, Adflex, Nylon, HDPE and PBT demonstrate that the invention is easily utilized by one skilled in the art to add further property-modifying aids as anticipated by the invention.

"Other Addition Types" illustrate that standard "processing" and property modifying aids such as Calcium Stearate and PVDF are also within the scope of the teachings of this invention. Since these two examples as so divergent in chemistry and properties, one skilled in the art will recognize that almost any material capable of being compounded into the extrusion process would provide an anticipated expansion of the variety of embodiments depending on the desired properties.

Definitions Relating to Processing Conditions

"Melt Temperature" and "Draw Temperature" are well known to those skilled in the art of extrusion and drawing of polymers. These, combined with the details of Example No. 1, provide detailed disclosure of the processing conditions utilized to successfully modify the TPE's of this invention.

"Draw Ratio" expresses the extent of orientation which occurs after the tape has been cooled through the water bath and then pulled across or through a heating element with each subsequent set of godets running a higher speeds. The difference in speed between the first godet pulling the tape out of the water cooling bath and the speed of the last godet is expressed as a ratio. In most fiber spinning and orienting processes, a considerable amount of the orientation occurs as the bundle of filaments are pulled by the first set of godets down the long air cooled channel, followed by additional drawing over heated rollers. One of the unique features of this invention is the use of high draw ratios to introduce an abnormally high degree of orientation into the elastomeric material which is retained at the end of the process. In other words, the elastomer is no longer elastic.

Definitions of Properties

"Break Strength" is the measure of the force required to break the resultant tape of the invention. Each example is expressed in the standard measure of "Newtons", since each tape varies in weight per length and dimensions.

"Elongation to Break" is measured at the same time the break strength or tenacity is measured. Since the modified thermoplastic elastomers of this invention have very low elastic limits, this measure primarily represents the additional, permanent deformation under stress which occurs before breaking.

"Elastic Limit" is the amount of "rubbery stretch" the product exhibits before the force exerted begins to deform the product. To measure this property, the tape is stretched until it will stretch no more without a major increase in force. This is the property most commonly exhibited by thermoplastic elastomer fibers like Spandex® or Lycra® or synthetic or natural rubber bands. After the TPE is modified according to the present invention, the normal 200–300% Elastic Limit of the Thermoplastic Elastomers are dramatically reduced to between about 0 and about 25%. See also, FIG. 3.

Definition of Dimensions

"Dimensions" are standard measures known to those skilled in the art. The Examples demonstrate that the nature of this invention provides an essentially limitless range of size and shape properties for the desired use as a dental floss.

Definitions Relating to Utility Factors

"Gentleness Perception" is the quantifying of the sensory property representing a lack of pain or irritation to the gums during use. Materials inflict pain in a variety of ways as they stimulate nerve endings and thus physical measurements, while informative, do not always directly correlate with sensory perception. While the perception of pain intensity will vary from individual to individual, it is common practice to normalize these variations by using individuals trained in recording their sensory perceptions on calibrated numeric scales. The scale we developed to evaluate the important user benefit of "gentleness" is similar to those used to evaluate malodor, harshness/softness of clothing, visual cleanliness of clothing, the intensity of sound or light, etc., etc. Obviously, normalizing the perceptions of individuals across a large number of trained observers increases the accuracy of the measurement, but in practical terms a well trained observer can reproducible detect differences of ±0.5 to 1 on the scale.

The Gentleness Index recorded under the "Gentleness Perception" column is specifically defined as follows:

On a scale of 1–10 the evaluators are instructed to "calibrate" what they perceive as "gentle on the gums during flossing" using their normal, personal flossing technique. They are instructed to arbitrarily assign what they feel as gentleness or lack thereof to selected, standard floss products.

a. The "most gentle" commonly known floss product (PTFE tape dental floss such as Glide®) is assigned a "Gentleness Index" of 8.0, b. a typical unwaxed multi-filament dental floss (J&J Waxed Mint) is assigned a Gentleness Index of 3.0 and c. a hard harsh tape of polypropylene is assigned a Gentleness Index of 1.0.

"Tape Flex-Twist Index" represents the physical measurement of one of the factors affecting gentleness, that of the propensity to "spring-back" or "snap" into the gums during use. While any one physical measure cannot totally evaluate gentleness, segregating this element allows the invention to be followed during the development and evaluation of a variety of embodiments. This index is easily described and reproduced.

a. A 20 cm section of the tape is suspended from a clamp and the lower end affixed to the center of a 15 cm steel bar having a weight of 30 grams.

b. The bar is twisted horizontally for 10 full rotations, introducing twist into the tape.

c. The bar is released, and the number of turns past the null point are counted.

This count of the rotations past the null point is the Tape Flex-Twist Index number.

While there are various flexibility indices commonly in use for polymeric substances, they are mostly useful for evaluating flexibility of larger dimensions than those tapes useful for dental floss. The unique feature of this index is that it measures the "damping" effect of the tape. This in turn correlates nicely with the perceived gentleness because the measure is effectively that of quantifying the reduction in the "wire-like" or "spring-like" properties of ordinary dental flosses and tapes. As the tape is used, and is constrained by the tight spaces between the teeth, the ability to "damp" the energy transferred to the gums becomes important. Should the dental floss "snap" without any "damping" of the energy required to insert the tape, the energy will be transferred to the nerve endings, producing more pain or less gentleness.

"Hardness—Shore D" is perhaps the most obvious standard measurement to apply to a polymeric tape as a function of gentleness. Table 3 illustrates effect of combining different tape materials with different coatings on the Shore D measurement. The microcrystalline wax on Glide® softens the total product slightly, for example, but the product of this invention coated with the non-crystalline coating has a much lower Shore D number, while the same un-coated PEBA tape is essentially the same as the PTFE tape with wax. This observation tracks use evaluation studies which demonstrate that the gentleness of the waxed PEBA tape of this invention is perceived to be equal to that of waxed PTFE tape. However, when coated with the non-crystalline coating, the PEBA tape is perceived as much gentler than either the waxed PTFE or waxed PEBA. Producing a modified TPE tape, which is as gentle as the PTFE is one desired objective of this invention and taken together, the Flex-Twist Index and Shore D provide useful predictors of gentleness.

TABLE 4

EXAMPLES
TAPE COMPOSITION

| Ex. No. | Thermoplastic Elastomer Type | Manufacturer | Trade name | Grade | Silicone Process Aid (%) | $TiO_2$ (%) | Secondary Polymer added Type (%) | Other Add'n Type (%) |
|---|---|---|---|---|---|---|---|---|
| 2 | PEBA polyester amide | Atofina | PEBAX | 55/33 | 3.5 | 1.8 | PP-4.7 | — |
| 3 | PEBA polyester amide | " | " | " | 3.5 | 1.8 | PP-4.7 Adflex-5 | — |
| 4 | PEBA polyester amide | " | " | " | 3.5 | 1.8 | PP-9.7 | — |
| 5 | PEBA polyester amide | Atofina | PEBAX | 63/33 | 0 | 0 | 0 | — |
| 6 | PEBA polyester amide | " | " | " | 0 | 1.8 | PP-1.2 | — |
| 7 | PEBA polyester amide | " | " | " | 3.5 | 1.8 | PP-4.7 | — |
| 8 | PEBA polyester amide | " | " | " | 3.5 | 1.8 | PP-4.7 Adflex-5 | — |
| 9 | PEBA polyester amide | " | " | " | 3.5 | 1.8 | PP-9.7 | — |
| 10 | PEBA polyester amide | " | " | " | 3.5 | 1.8 | PP-4.7 Nylon 11-5 | — |
| 11 | TPE polyether ester | DuPont | Hytrel | 6359FG | 2.3 | 1.0 | 0 | Ca Stearate 0.1 |
| 12 | TPE polyether ester | " | " | " | 3.5 | 1.8 | PP-4.7 | Ca Stearate 0.1 |
| 13 | TPE-E polyether ester | DSM | Amitel | PMS81 | 0 | 0 | 0 | — |
| 14 | TPE-E polyether ester | " | " | " | 0 | 1.8 | PP-1.2 | — |
| 15 | TPE-E polyether ester | " | " | " | 3 | 0 | PBT-5 | — |
| 16 | TPE-E polyether ester | " | " | " | 0 | 0 | PBT-5 | — |
| 17 | TPE-E polyether ester | " | " | " | 0 | 1.8 | PP-1.2 PBT-5 | — |

| | PROCESSING CONDITIONS | | PROPERTIES | | DIMENSIONS | | | UTILITY FACTORS | | |
|---|---|---|---|---|---|---|---|---|---|---|
| Ex. No. | Melt Temp °C. | Draw Temp °C. | Draw Ratio | Break Strength in Newtons | Elongation to Break (%) | Elastic Limit (%) | Decitex | Width (mm) | Thick (mm) | Gentleness Perception | Tape Flex Twist Index | Hardness Shore D |
| 2 | 260 | 130 | 6.8:1 | 30 | 26 | 0 | 750 | 1.30 | 0.063 | 6 | 4 | 37 |
| 3 | 260 | 130 | 6.5:1 | 27 | 18 | 0 | 760 | 1.30 | 0.063 | 6 | 4 | 37 |
| 4 | 260 | 130 | 6.8:1 | 26 | 19 | 0 | 760 | 1.30 | 0.063 | 6 | 4 | 37 |
| 5 | 260 | 135 | 6:1 | 30 | 15 | 0 | 805 | 1.44 | 0.065 | 5.5 | 4 | 36 |
| 6 | 260 | 135 | 6.3:1 | 32.36 | 13 | 0 | 800 | 1.41 | 0.067 | 5.5 | 4 | 36 |
| 7 | 260 | 135 | 6.2:1 | 33.47 | 17 | 0 | 860 | 1.36 | 0.066 | 5.5 | 4 | 36 |
| 8 | 260 | 135 | 6.2:1 | 25.94 | 14 | 0 | 810 | 1.32 | 0.078 | 5.5 | 4 | 36 |
| 9 | 260 | 135 | 6.2:1 | 29.46 | 14 | 0 | 780 | 1.34 | 0.069 | 5.5 | 4 | 36 |
| 10 | 260 | 135 | 6.2:1 | 30.63 | 13 | 0 | 810 | 1.30 | 0.065 | 5.5 | 4 | 36 |
| 11 | 225 | 130 | 5:1 | 20 | 20 | 15 | 1400 | 1.70 | 0.070 | 7 | 3 | 33 |
| 12 | 225 | 140 | 5.7:1 | 24 | 14 | 10 | 1230 | 1.70 | 0.070 | 7 | 3 | 33 |
| 13 | 235 | 140 | 4.3:1 | 18 | 13 | 10 | 1500 | 1.63 | 0.084 | 7 | 3 | 33 |
| 14 | 240 | 115 | 4.3:1 | 19 | 14 | 5 | 1634 | 1.64 | 0.085 | 7 | 3 | 33 |
| 15 | 235 | 140 | 4.3:1 | 19 | 10 | 3 | 1580 | 1.68 | 0.079 | 7 | 3 | 33 |
| 16 | 235 | 140 | 4.3:1 | 18 | 12 | 2 | 1500 | 1.70 | 0.086 | 7 | 3 | 33 |
| 17 | 235 | 140 | 4.3:1 | 21 | 15 | 4 | 1575 | 1.77 | 0.083 | 7 | 3 | 33 |

TABLE 5

TAPE COMPOSITION

| Ex. No. | Thermoplastic Elastomer Type | Manufacturer | Trade name | Grade | Silicone Silicone Aid (%) | TiO₂ (%) | Secondary Polymer added Type (%) | Other Add'n Type (%) |
|---|---|---|---|---|---|---|---|---|
| 18 | TPE-E polyether ester | DSM | Arnitel | EM550 | 0 | 0 | 0 | — |
| 19 | TPE-E polyether ester | " | " | " | 0 | 1.8 | PP-1.2 | — |
| 20 | TPE-E polyether ester | " | " | " | 0 | 1.8 | PP-6.2 | — |
| 21 | TPE-E polyether ester | " | " | " | 0 | 0 | PBT-5 | — |
| 22 | TPE-P polyether ester | OSM | Arnitel | EM630 | 0 | 0 | 0 | — |
| 23 | TPE-P polyether ester | " | " | " | 0 | 1.8 | PP-1.2 | — |
| 24 | TPE-P polyether ester | " | " | " | 0 | 1.8 | PP-1.2 | Adflex - 5 |
| 25 | TPE-P polyether ester | " | " | " | 0 | 1.8 | PP-6.2 | — |
| 26 | TPE-P polyether ester | " | " | " | 0 | 0 | PBT-5 | — |
| 27 | TPE-P polyester ester | DSM | Arnitel | UM552 | 0 | 0 | 0 | — |
| 28 | TPE-P polyester ester | " | " | " | 0 | 0 | 0 | Ca Stearate 0.1 |
| 29 | TPE-P polyester ester | " | " | " | 0 | 1.8 | PP-1.2 | — |
| 30 | TPE-P polyester ester | " | " | " | 0 | 0 | Adflex-5 | — |
| 31 | TPE-P polyester ester | " | " | " | 0 | 1.5 | PP-1.2 PBT-5 | Ca Stearate 0.1 |
| 32 | TPE-P polyester ester | " | " | " | 0 | 0 | PBT-5 | Ca Stearate 0.1 |
| 33 | EPDM TPV | Monteil | Adflex | Q100F | 0 | 0 | PP-20 | — |
| 34 | EPDM TPV | " | " | " | 3.5 | 1.8 | PP-24.7 | — |
| 35 | EPDM TPV | " | " | " | 7 | 3 | PP-30 | — |
| 36 | EPDM TPV | " | " | " | 7 | 3 | PP-34.7 | — |
| 37 | EPDM TPV | " | " | " | 7 | 3 | PP-40 | — |

| | PROCESSING CONDITIONS | | PROPERTIES | | | DIMENSIONS | | | UTILITY FACTORS | | |
|---|---|---|---|---|---|---|---|---|---|---|---|
| Ex. No. | Melt Temp °C. | Draw Temp °C. | Draw Ratio | Break Strength in Newtons | Elongation to Break (%) | Elastic Limit (%) | Decitex | Width (mm) | Thick (mm) | Gentleness Perception | Tape Flex Twist Index | Hardness Shore D |
| 18 | 240 | 140 | 4.3:1 | 23 | 25 | 7 | 1800 | 1.95 | 0.096 | 7 | 3 | 33 |
| 19 | 240 | 115 | 6:1 | 27 | 11 | 5 | 1050 | 1.47 | 0.071 | 7 | 3 | 33 |
| 20 | 240 | 140 | 5.6:1 | 26 | 17 | 5 | 1216 | 1.45 | 0.071 | 7 | 3 | 33 |
| 21 | 240 | 145 | 5.9:1 | 28 | 145 | 5 | 1220 | 1.55 | 0.074 | 7 | 3 | 33 |
| 22 | 235 | 150 | 4.5:1 | 18 | 12 | 4 | 1090 | 1.44 | 0.067 | 7 | 3 | 33 |
| 23 | 235 | 150 | 4.7:1 | 17 | 11 | 4 | 1130 | 1.50 | 0.068 | 7 | 3 | 33 |
| 24 | 235 | 150 | 4.6:1 | 18 | 10 | 7 | 961 | 1.35 | 0.065 | 7 | 3 | 33 |
| 25 | 235 | 150 | 4.6:1 | 14 | 30 | 10 | 965 | 1.24 | 0.073 | 7 | 3 | 33 |
| 26 | 235 | 150 | 4.6:1 | 20 | 12 | 5 | 1018 | 1.39 | 0.069 | 7 | 3 | 33 |
| 27 | 240 | 150 | 6.6:1 | 32 | 12 | 8 | 1300 | 1.49 | 0.070 | 7.5 | 3.5 | 31 |
| 28 | 230 | 150 | 5.6:1 | 26 | 15 | 8 | 1090 | 1.40 | 0.070 | 7.5 | 3.5 | 31 |
| 29 | 240 | 150 | 6.3:1 | 29 | 16 | 8 | 1150 | 1.46 | 0.070 | 7.5 | 3.5 | 31 |
| 30 | 230 | 140 | 5.6:1 | 30 | 16 | 10 | 1233 | 1.48 | 0.069 | 7.5 | 3.5 | 31 |
| 31 | 230 | 145 | 5.7:1 | 22 | 19 | 10 | 1108 | 1.53 | 0.067 | 7.5 | 3.5 | 31 |
| 32 | 230 | 245 | 5.3:1 | 24 | 14 | 8 | 1143 | 1.48 | 0.064 | 7.5 | 3.5 | 31 |
| 33 | 240 | 130 | 4.5:1 | 26 | 20 | 0 | 910 | 1.60 | 0.064 | 5.5 | NT | NT |
| 34 | 240 | 130 | 4.5:1 | 25 | 24 | 0 | 940 | 1.59 | 0.064 | 5.5 | NT | NT |
| 35 | 240 | 130 | 4.7:1 | 28 | 20 | 0 | 870 | 1.58 | 0.064 | 5.5 | NT | NT |
| 36 | 240 | 130 | 4.7:1 | 27 | 23 | 0 | 880 | 1.58 | 0.060 | 5.5 | NT | NT |
| 37 | 240 | 130 | 4.7:1 | 35 | 18 | 0 | 720 | 1.44 | 0.063 | 5 | NT | NT |

The following examples (38 through 59) as detailed in Tables 6 and 7 further illustrate modifiable thermoplastic elastomers suitable for use as dental tapes of the present invention.

TABLE 6

Illustrative Examples
TAPE COMPOSITION

| Ex. No. | Thermoplastic Elastomer Type | Manufacturer | Trade name | Grade | Silicone Process Aid (%) | TiO$_2$ (%) | Secondary Polymer added Type (%) | Other Add'n Type (%) |
|---|---|---|---|---|---|---|---|---|
| 38 | PEBA polyester amide | Atofina | PEBAX | 55133 | 0 | 1.8 | PP-1.2 | — |
| 39 | PEBA polyester amide | " | " | " | 3.5 | 1.8 | PP-4.7 EMA-3 | — |
| 40 | PEBA polyester amide | " | " | " | 3.5 | 1.8 | PP-4.7 | — |
| 41 | PEBA | Atofina | PEBAX | 63/33 | 3.5 | 1.8 | PP-4.7 EMA-3 | — |
| 42 | " | " | " | " | 0 | 0 | Nylon 11-5 | PDVF-3 |
| 43 | TPE-E polyether ester | DSM | Arnitel | PM581 | 3 | 0 | 0 | — |
| 44 | TPE-E polyether ester | DSM | Amitel | EM550 | 3 | 0 | 0 | — |
| 45 | TPE-E polyether ester | " | " | " | 3 | 1.8 | PP-1.2 EMA-3 | — |
| 46 | TPE-E polyether ester | DSM | Arnitel | UM552 | 3 | 1.8 | PP-1.2 | — |

| | PROCESSING CONDITIONS | | PROPERTIES | | DIMENSIONS | | | UTILITY FACTORS | | | |
|---|---|---|---|---|---|---|---|---|---|---|---|
| Ex. No. | Melt Temp °C. | Draw Temp °C. | Draw Ratio | Break Strength in Newtons | Elongation to Break (%) | Elastic Limit (%) | Decitex | Width (mm) | Thick (mm) | Gentleness Perception | Tape Flex Twist Index | Hardness Shore D |
| 38 | 260 | 130 | 6.8:1 | 28 | 24 | 0 | 775 | 1.30 | 0.063 | 6 | 4 | 37 |
| 39 | 260 | 130 | 7:1 | 28 | 30 | 3 | 750 | 1.30 | 0.063 | 8 | 4 | 37 |
| 40 | 260 | 130 | 6.8:1 | 29 | 24 | 0 | 800 | 1.35 | 0.070 | 6 | 4 | 37 |
| 41 | 260 | 135 | 6.5:1 | 31 | 20 | 3 | 800 | 1.40 | 0.065 | 5.5 | 4 | 36 |
| 42 | 260 | 135 | 6.2:1 | 28 | 14 | 0 | 800 | 1.30 | 0.065 | 5.5 | 4 | 36 |
| 43 | 235 | 140 | 5:1 | 22 | 16 | 7 | 1400 | 1.60 | 0.079 | 7 | 3 | 33 |
| 44 | 240 | 140 | 6:1 | 25 | 20 | 7 | 800 | 1.30 | 0.060 | 7 | 3 | 33 |
| 45 | 240 | 140 | 6:1 | 27 | 15 | 5 | 850 | 1.35 | 0.065 | 7 | 3 | 33 |
| 46 | 240 | 150 | 6:1 | 27 | 17 | 10 | 1100 | 1.47 | 0.069 | 7.5 | 3 | 33 |

TABLE 7

EXAMPLES
TAPE COMPOSITION

| Ex. No. | Thermoplastic Elastomer Type | Manufacturer | Trade name | Grade | Silicone Process Aid (%) | TiO$_2$ (%) | Secondary Polymer added Type (%) | Other Add'n Type (%) |
|---|---|---|---|---|---|---|---|---|
| 47 | Styrenics SEBS | Alphagary | Evoprene | G978 | 0 | 1.8 | PP-1.2 | — |
| 48 | Styrenics SEBS | " | " | " | 3 | 1.8 | PP-1.2 | — |
| 49 | Styrenics SEBS | " | " | " | 0 | 1.8 | PP-1.2 EMA-3 | — |
| 50 | Styrenics SEBS | " | " | " | 3.5 | 1.8 | PP-9.7 | — |
| 51 | Styrenics SEBS | " | " | " | 3.5 | 1.8 | PP-9.7 PS-5 | — |
| 52 | TPU 90AEN | Dow | Pelethane | 2103- | 0 | 1.8 | PP-1.2 | — |
| 53 | TPU 90AEN | " | " | " | 3 | 1.8 | PP-1.2 | — |

TABLE 7-continued

EXAMPLES
TAPE COMPOSITION

| Ex. | | | | | | | | | |
|---|---|---|---|---|---|---|---|---|---|
| 54 | TPU 90AEN | " | " | " | 0 | 1.8 | PP-1.2 EMA-3 | — |
| 55 | TPU 90AEN | " | " | " | 3.5 | 1.8 | PP-9.7 | — |
| 56 | TPV | DSM | Sarlink | 4149D | 0 | 1.8 | PP-1.2 | — |
| 57 | " | " | " | " | 3 | 1.8 | PP-1.2 | — |
| 58 | " | " | " | " | 0 | 1.8 | PP-1.2 EMA-3 | — |
| 59 | " | " | " | " | 3 | 1.8 | PP-6.2 | — |

| | PROCESSING CONDITIONS | | | PROPERTIES | | DIMENSIONS | | | UTILITY FACTORS | | |
|---|---|---|---|---|---|---|---|---|---|---|---|
| Ex. No. | Melt Temp °C. | Draw Temp °C. | Draw Ratio | Break Strength in Newtons | Elongation to Break (%) | Elastic Limit (%) | Decitex | Width (mm) | Thick (mm) | Gentleness Perception | Tape Flex Twist Index | Hardness Shore D |
| 47 | 200 | 100 | 7:1 | 19 | 30 | 10 | 1100 | 1.30 | 0.060 | 6 | 4 | 37 |
| 47 | 200 | 100 | 7:1 | 19 | 30 | 10 | 1100 | 1.30 | 0.060 | 6 | 4 | 37 |
| 48 | 200 | 100 | 7:1 | 20 | 35 | 12 | 1100 | 1.30 | 0.060 | 6 | 4 | 37 |
| 49 | 200 | 100 | 7.2:1 | 17 | 32 | 12 | 1100 | 1.30 | 0.060 | 6 | 4 | 37 |
| 50 | 200 | 100 | 7:1 | 14 | 20 | 7 | 1100 | 1.30 | 0.060 | 8 | 4 | 37 |
| 51 | 200 | 100 | 7:1 | 22 | 28 | 8 | 1100 | 1.30 | 0.060 | 6 | 4 | 37 |
| 52 | 230 | 120 | 7:1 | 32 | 15 | 5 | 1200 | 1.40 | 0.068 | 7 | 3 | 33 |
| 53 | 230 | 120 | 6:1 | 30 | 17 | 6 | 1200 | 1.40 | 0.068 | 7 | 3 | 33 |
| 54 | 230 | 120 | 6:1 | 26 | 16 | 6 | 1200 | 1.40 | 0.068 | 7 | 3 | 33 |
| 55 | 230 | 120 | 5:1 | 22 | 10 | 2 | 1300 | 1.45 | 0.070 | 7 | 3 | 33 |
| 56 | 220 | 105 | 4.5:1 | 20 | 20 | 5 | 1400 | 1.45 | 0.072 | 6 | 4 | 37 |
| 57 | 220 | 105 | 5:1 | 22 | 35 | 7 | 1300 | 1.40 | 0.070 | 6 | 4 | 37 |
| 58 | 220 | 105 | 4.8:1 | 19 | 20 | 5 | 1350 | 1.48 | 0.075 | 6 | 4 | 37 |
| 59 | 220 | 105 | 4.2:1 | 15 | 20 | 5 | 1450 | 1.48 | 0.075 | 6 | 4 | 37 |

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

What is claimed is:

1. Oriented thermoplastic elastomer based dental tapes extruded with melt spinning extrusions carried out at draw ratios from between about 4:1 and about 7.5:1, and draw temperatures from between about 80° and about 265° C., wherein said oriented tapes have the following physical properties:

an elongation at break of less than about 50%, and
an elastic limit of less than about 25%,
and where said thermoplastic elastomer is selected from the group consisting of styrenics, olefinic blends, elastomeric alloys, urethanes, copolyesters, polyamides and mixtures and/or copolymers thereof.

2. The oriented thermoplastic elastomer based dental tapes of claim 1, further having a tape flex-twist index from between about 2.5 and about 5, and wherein a processing additive is employed in said melt spinning extrusion.

3. The oriented thermoplastic elastomer based dental tapes of claim 2, wherein the processing additive is selected from the group consisting of ultra-high molecular weight polydimethylsiloxanes in organic resin carriers, copolymers, calcium stearate and mixtures thereof.

4. The oriented thermoplastic elastomer based dental tapes of claim 3, wherein the organic resin carrier for said processing additive is selected from the group consisting of: polypropylene, polybutylene terephthalate, ethylene maleic acid, high density polyethylene, nylon and mixtures thereof.

5. The oriented thermoplastic elastomer based dental tapes of claim 1, further having the following physical properties:

a break strength from between about 10 Newtons and about 40 Newtons,
a gentleness perception from between about 5 and about 8,
a Shore D hardness from between about 30 and about 40, and
a tape flex-twist index from between about 2.5 and about 5.

6. The oriented thermoplastic elastomer based dental tapes of claim 1, wherein the polyamides are selected from the group of structural formulas consisting of:

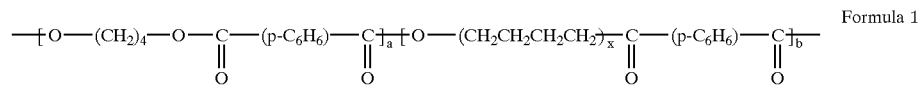

Formula 1 wherein: a=16 to 40, x=10 to 50, and b=16 to 40;

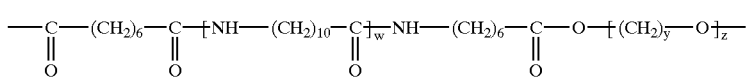

Formula 2

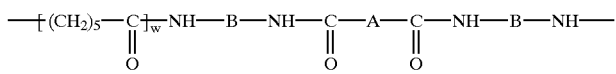

Formula 3

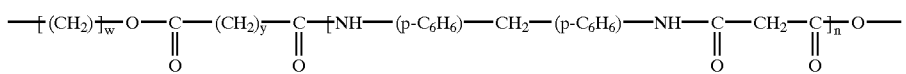

Formula 4 wherein A is a $C_{19}$ to $C_{21}$ dicarboxylic acid and wherein B is:

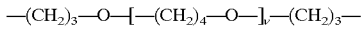

and wherein n, v, w, y and z are whole numbers; and

Formula 5 where PA represents the polyamide segment and PE the polyether segment and n is a whole number.

7. The oriented thermoplastic elastomer based dental tapes of claim 1, wherein sent invention comprise a polyamide having the structural Formula 1:

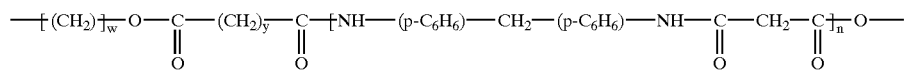

wherein: a and b=16 to 40 and x=16 to 50.

8. The oriented thermoplastic elastomer based dental tapes of claim 1, wherein the thermoplastic elastomer is a polyamide having the structural Formula 2:

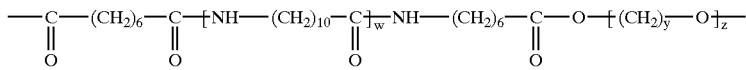

wherein w and z are whole numbers.

9. The oriented thermoplastic elastomer based dental tapes of claim 1, wherein the thermoplastic elastomer is a polyamide having the structural Formula 3:

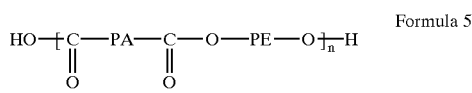

wherein
A=$C_{19}$ to $C_{21}$ dicarboxylic acid and
B=—$(CH_2)_3$—O—[$(CH_2)_4$—O—]$_v$—$(CH_2)_3$—.

10. The oriented thermoplastic elastomer based dental tapes of claim 1, wherein the thermoplastic elastomer is a polyamide having the structural Formula 4:

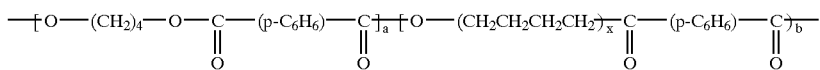

wherein n, y and w are whole numbers.

11. The oriented thermoplastic elastomer based dental tapes of claim 1, wherein the thermoplastic elastomer is a polyamide having the structural Formula 5:

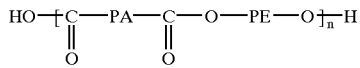

where PA represents the polyamide segment and PE the polyether segment and n is a whole number.

12. The oriented thermoplastic elastomer based dental tapes of claim 1, used to deliver substantive, flake-free, saliva soluble coatings to interproximal and subgingival sites during flossing.

13. The oriented thermoplastic elastomer based dental tapes of claim 1, coated with substantive, crystal-free coatings having Shore D hardness substantially lower than commercial dental tapes.

14. The oriented thermoplastic elastomer based dental tapes of claim 1, further having the physical property of an elastic limit up to about 15%.

15. The oriented thermoplastic elastomer based dental tapes of claim 1, further having the physical property of a tape flex-twist index from between about 2.5 and about 5.

16. The oriented thermoplastic elastomer based dental tapes of claim 1, further comprising a coating with a substantive, saliva soluble, crystal-free material or combination of materials that are substantially flake-free, wherein said coatings are substantially totally released interproximally and subgingivally during flossing.

17. A method for the melt spinning extrusion of oriented thermoplastic elastomer based dental tapes comprising the steps of:

a. melting said thermoplastic at melt temperatures ranging from between about 170° C. and about 300° C., b. compressing said melt through suitable sized tape-shape holes in a melt spinning extruder, c. taking up said tape at a spinning speed while passing said tape through a cooling bath, and d. drawing said cooled tape at draw ratios from between about 4:1 and about 7.5:1 at draw temperatures from between about 80° C. and about 265° C.

18. The method of claim 17, which further comprises the step of extruding through a melt spinning extruder in which tape-shaped holes are selected from holes having a width from between about 1.05 mm and about 2.15 mm and a thickness from between about 0.05 mm and about 0.09 mm, whereby tapes produced from these holes have a decitex from between about 700 and about 1700.

* * * * *

UNITED STATES PATENT AND TRADEMARK OFFICE
CERTIFICATE OF CORRECTION

PATENT NO.    : 6,591,844 B2
DATED         : July 15, 2003
INVENTOR(S)   : David Barlow et al.

It is certified that error appears in the above-identified patent and that said Letters Patent is hereby corrected as shown below:

<u>Title page,</u>
Item [73], should read -- Assignee: Peri-Dent Limited, Scotland (GB) --

Signed and Sealed this

Fourteenth Day of October, 2003

JAMES E. ROGAN
*Director of the United States Patent and Trademark Office*